United States Patent [19]

Iida

[11] Patent Number: 4,889,485
[45] Date of Patent: Dec. 26, 1989

[54] ORTHODONTIC APPARATUS FOR ATTACHMENT TO A TOOTH

[75] Inventor: Eiji Iida, Okhuma, Japan

[73] Assignee: GAC International, Inc., Central Islip, N.Y.

[21] Appl. No.: 188,049

[22] Filed: Apr. 29, 1988

[30] Foreign Application Priority Data

Apr. 30, 1987 [JP] Japan .................................. 62-107589

[51] Int. Cl.⁴ ............................................... A61C 7/00
[52] U.S. Cl. ........................................................ 433/9
[58] Field of Search ........................................ 433/8, 9

[56] References Cited

U.S. PATENT DOCUMENTS 4,068,379 1/1978 Miller et al. .............................. 433/9
4,165,561 8/1979 Miller et al. .............................. 433/9

Primary Examiner—Robert Peshock
Attorney, Agent, or Firm—Kenyon & Kenyon

[57] ABSTRACT

An orthodontic apparatus for attachment to a tooth has a base portion, a base plate attached to the base portion and a plurality of layers of mesh material superimposed on the outer surface of the base plate and attached thereto. The apparatus is attachable to the surface of a tooth by applying an adhesive material to the plurality of layers of mesh material and bonding the mesh material directly to the surface of the tooth.

21 Claims, 3 Drawing Sheets

ORTHODONTIC APPARATUS FOR ATTACHMENT TO A TOOTH

FIELD OF THE INVENTION

The invention relates to orthodontic apparatus, and more particularly, is directed to apparatus such as orthodontic brackets, buccal tubes and lingual appliances having an improved construction for attachment to a tooth.

BACKGROUND INFORMATION

Orthodontic brackets for direct bonding to a tooth are well known and typically include a body portion defining a slot in the front surface thereof for holding an archwire. Wing portions of the bracket project outwardly for attaching ligature wire thereto for securing the archwire to the bracket.

A base plate of the bracket is attached to the bottom of the base portion in a conventional manner. In certain brackets it is known to include a single layer of mesh material which is in turn, superimposed on the base plate, and attached thereto. The bracket is mounted to a tooth by applying adhesive to the mesh layer which is pressed against the surface of the tooth. The layer of mesh material improves the strength of the bond between the bracket and the tooth by imparting what is termed an "undercut effect" to the back surface of the base plate.

One problem associated with brackets using the single layer of mesh material, is that the system provides a relatively weak bond between the bracket and the tooth. Additionally, when the bracket body is pulled from the tooth surface during, or after treatment, the single layer mesh construction and the large openings in the mesh material cause a large quantity of adhesive material to remain on the surface of the tooth As a result, a great deal of labor is required to remove the remaining adhesive and to polish the surface of the tooth. This problem is particularly troublesome sometimes when the adhesive removed from the tooth results in damage to the enamel of the tooth.

It is an object of the present invention therefore to provide an orthodontic apparatus for mounting to a tooth that overcomes the above-mentioned drawbacks and disadvantages of known apparatus.

It is a further object of the invention to provide an apparatus for mounting to a tooth that provides an increased bonding strength between the bracket and the tooth over known apparatus.

It is yet a further object of the invention to provide an apparatus for mounting to a tooth that leaves only a small quantity of adhesive material on the surface of the tooth when the apparatus is removed from the tooth.

Other objects and advantages of the invention will become apparent in view of the following detailed description and drawings taken in connection therewith.

SUMMARY OF THE INVENTION

The present invention is directed to an orthodontic apparatus for attachment to a tooth. The apparatus of the invention comprises a base portion, a base plate attached to the base portion and a plurality of layers of mesh material superimposed on the outer surface of the base plate and attached thereto. The apparatus is attached to the surface of a tooth by applying an adhesive material to the plurality of layers of mesh material and bonding the layers of mesh material to the surface of the tooth.

In one apparatus of the invention each successive layer of mesh material in the direction from the base plate to the outermost layer of mesh material is rougher than the mesh of the preceding layer of mesh material.

Another apparatus of the invention comprises three layers of mesh material wherein the first layer of mesh material is attached to the base plate and the third layer of mesh material is the outermost layer.

In yet another apparatus of the invention comprising three layers of mesh material, the first layer of mesh material is 300 to 400 mesh, the second layer of mesh material is approximately 200 mesh, and the third layer of mesh material is approximately 100 mesh.

The several layers of mesh material of the apparatus of the invention provide an increased bonding strength between the bracket and the tooth over known apparatus, and upon removal of the bracket from the tooth, the layers of mesh material permit only minute portions of adhesive material to remain on the tooth.

DESCRIPTION OF PREFERRED EMBODIMENTS

Figure 1:
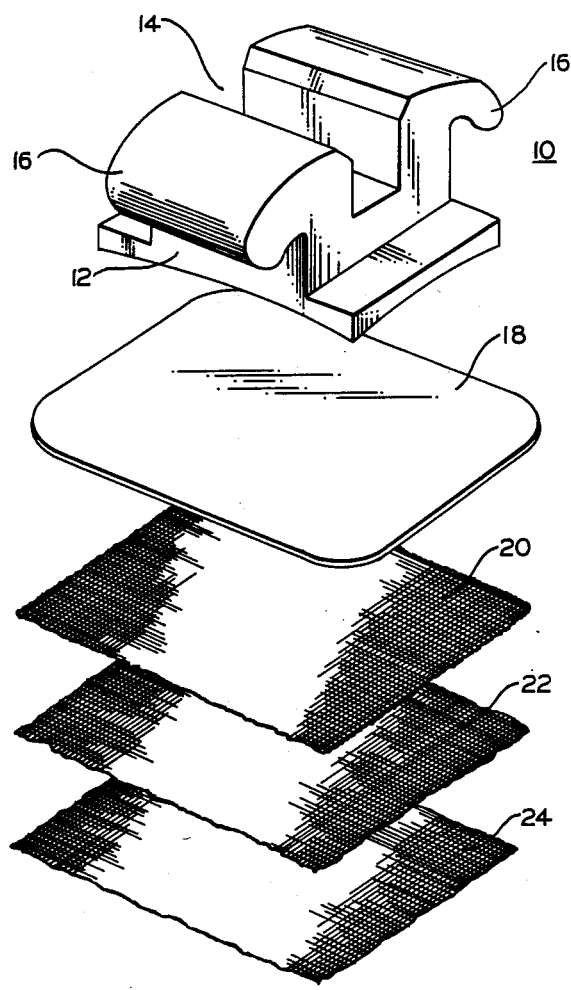
FIG. 1 is an exploded perspective view of an orthodontic apparatus for attachment to a tooth embodying the invention.

In FIG. 1, a preferred embodiment of an orthodontic bracket embodying the invention is illustrated 10. The bracket 10 comprises a base portion 12, an archwire slot 14 defined in the front face thereof for holding an archwire, and a pair of wing portions 16, 16 for the attachment of ligature wire thereto, not shown, for holding the archwire in place. A metal base plate 18 of the bracket is attached to the bottom of the base portion 12 in a conventional manner.

The bracket 10 further comprises a plurality of layers of mesh material including a first layer of mesh material 20, a second layer of mesh material 22 and a third layer of mesh material 24. The first layer of mesh material 20 is superimposed on the outer surface of the base plate 18 and is attached thereto. The second layer of mesh material 22 and third layer of mesh material 24 are superimposed on one another and, in turn, superimposed on the outer surface of first layer 20 and attached thereto. The layers of mesh material are attached to one another and to the base plate 18 in a conventional manner, such as, for example, by diffusion welding.

The bracket 10 is mounted to the surface of a tooth by applying a known adhesive material, not shown, to the outer surface of the third layer of mesh material 24. The adhesive coated surface of the bracket 10 is then pressed against the surface of the tooth, not shown, and held in place until the adhesive material is cured. The several layers of mesh material 20, 22 and 24 permit the adhesive material to flow therethrough and accordingly, increase the strength of the bond between the adhesive material and the bracket 10.

The layers of mesh material 20, 22 and 24 are preferably made of stainless steel wire mesh and in this embodiment, each layer of mesh material is 400 mesh, which has far more narrow openings than for instance the 100 mesh material employed in known devices.

Figure 2A:
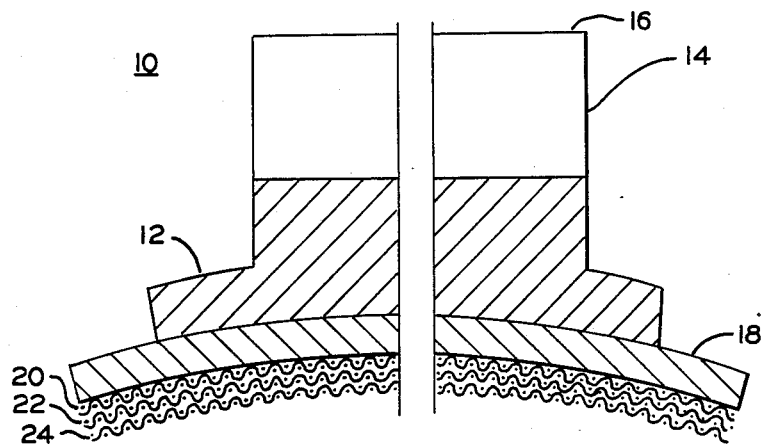
FIG. 2A is a cross-sectional view of the apparatus of FIG. 1 shown assembled.
Figure 2B:
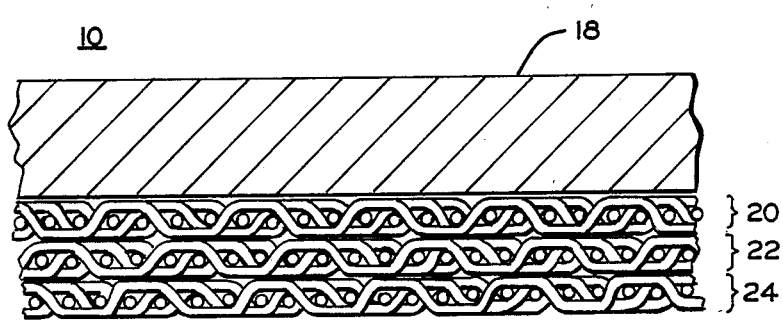
FIG. 2B is a partial cross-sectional view of another embodiment of the apparatus of the invention illustrating a twill type of mesh material.
Figure 2C:
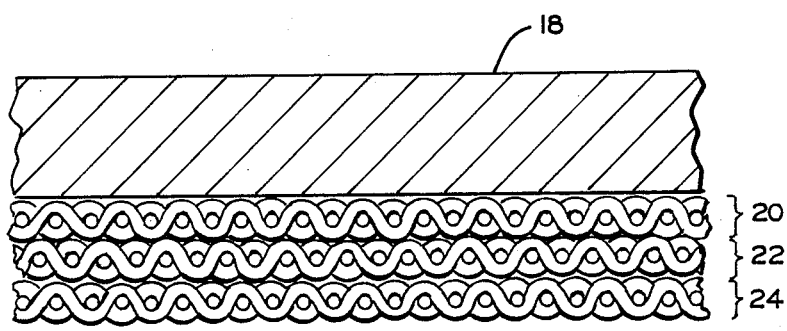
FIG. 2C is a partial cross-sectional view of another embodiment of the apparatus of the invention illustrating a plain fabric type of mesh material.

The type of mesh material employed in the bracket 10 is either the twill type wherein the stainless steel warp wire and woof wire are joined in two straddles, as shown in FIG. 2B, or the plain fabric type wherein the warp wire and woof wire are alternately joined as shown in FIG. 2C. The preferred embodiments shown in FIGS. 2B and 2C will be described in further detail below. Although different types of mesh material can be effectively employed, the twill and plain fabric types have proven to be most effective in imparting an undercut effect to increase the strength of the bond between the bracket and a tooth.

It has also been found that the mechanical strength of the bond between the adhesive material and each layer of mesh material can be substantially increased by varying the type of mesh material with the different layers of mesh. For example, a plain fabric type mesh may be employed for the first and second layers of mesh material 20 and 22, whereas a twill type mesh may be used for the third layer of mesh material 24, which is directly bonded to the surface of a tooth. On the other hand, a twill type mesh may be employed for the first and second layers of mesh material 20 and 22, and a plain fabric type mesh for the third layer of mesh material 24. In either case, the mechanical strength of the bond between the adhesive material and layers of mesh material is increased as compared to the case where only one type of mesh material is employed.

The orthodontic bracket 10 is constructed by mounting the base plate 18 to the bottom of the base portion 12 and attaching it thereto in a conventional manner. As shown in FIG. 2A, the base plate 18 is manufactured with a curved configuration in order to mate with the bottom surface of the base portion 12. The layers of mesh material 20, 22 and 24 are then superimposed on one another and on the outer surface of the base plate 18 and attached thereto in a conventional manner, such as by diffusion welding. The exact order of combining the components of the bracket 10 may be varied. For example, the layers of mesh material 20, 22 and 24 can be first superimposed on, and attached to a large sheet of base plate material which is in turn, cut into individual base plates 18. Each base plate 18 and attached layers of mesh material 20, 22 and 24 are then attached to a base portion 12 of an orthodontic bracket. The latter method of construction may be more desirable since it is more convenient to attach the several layers of mesh material 20, 22 and 24 to a large sheet of base plate material rather than attach them to an individual base plate 18. In any event, the three layers of mesh material 20, 22 and 24, preferably 400 mesh, are substantially finer than that employed in known devices and cause the bracket of the invention to substantially increase the undercut effect and thus increase the strength of the bond between the bracket 10 and the surface of a tooth.

The several layers of mesh material of the bracket 10 increase the bonding area for the adhesive material in comparison to known devices employing only a single layer of mesh material and accordingly, increase the strength of the bond between the bracket 10 and the tooth. Furthermore, the construction of the bracket 10 also permits only minute amounts of adhesive material to remain on the surface of the tooth upon removal of the bracket therefrom. The several layers of mesh material fractionate the adhesive material into minute portions so that upon removal of the bracket 10 from a tooth, any adhesive material remaining on the surface of the tooth is in tiny portions that can be easily removed from the tooth without the threat of damage thereto. Accordingly, the labor required in removing adhesive material and polishing the surface of the tooth after removal of the bracket 10 is greatly reduced as compared to that associated with the use of known devices.

Turning to FIGS. 2B and 2C, further embodiments of the base plate 18 and layers of mesh material 20, 22 and 24 of the bracket 10 are shown. The layers of mesh material are superimposed on one another and attached to the base plate in the same manner as described above in relation to FIGS. 1 and 2 for the previous embodiment. However, the first layer of mesh material 20 is 100 mesh, the second layer of mesh material 22 is 200 mesh, and the third layer of mesh material 24 is 300 to 400 mesh. As heretofore described, FIG. 2B illustrates a twill type of mesh material whereas FIG. 2C illustrates a plain fabric type of mesh material.

The bracket 10 of either FIGS. 2B or 2C therefore is constructed so that the openings of the mesh material become narrower from the base plate 18 to the outer layer of mesh material 24. It is also possible with the embodiments shown in FIGS. 2B and 2C, to vary the types of mesh material with the different layers of mesh in order to increase the strength of the bond between the adhesive material and the layers of mesh material, as described above in relation to FIGS. 1 and 2 for the previous embodiment.

Figure 3:
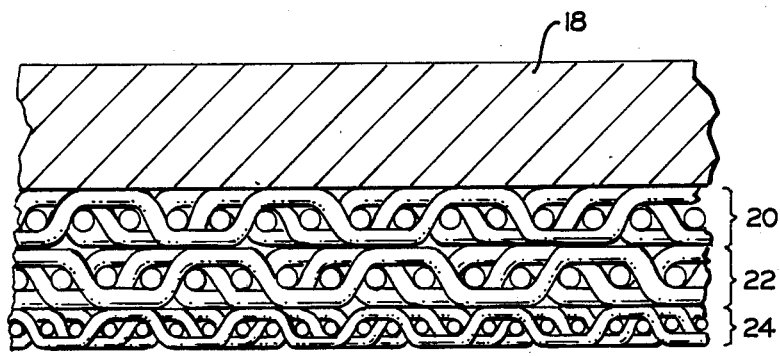
FIG. 3 is a partial cross-sectional view of another embodiment of the apparatus of the invention wherein the outer layer of mesh material has a finer mesh than the interior layers of mesh material.

Turning to FIG. 3 another embodiment of the base plate 18 and layers of mesh material 20, 22 and 24 of the bracket 10 is shown. The layers of mesh material are superimposed on one another and attached to the base plate in the same manner as described above in relation to the previous embodiments. As can be seen, the bracket of FIG. 3 employs a twill type of mesh material. However, the first and second layers of mesh material 20 and 22 are 100 to 200 mesh, and the third layer of mesh material 24 is 300 to 400 mesh.

Figure 4:
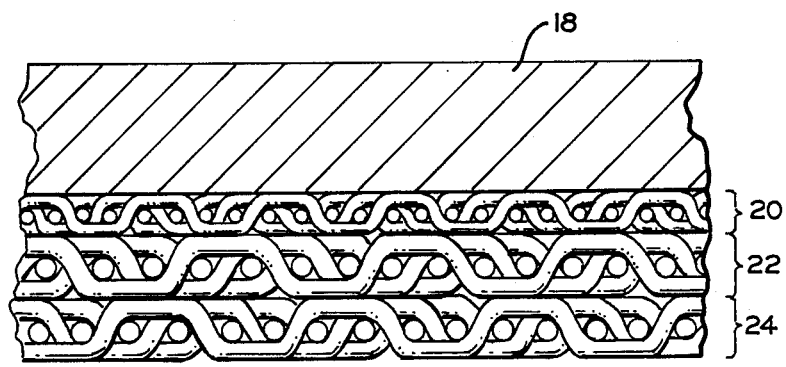
FIG. 4 is a partial cross-sectional view of another embodiment of the apparatus of the invention wherein the outer layer of mesh material has a rougher mesh than the interior layers of mesh material.

Turning to FIG. 4 another embodiment of the base plate 18 and layers of mesh material 20, 22 and 24 of the bracket 10 is shown. The layers of mesh material are superimposed on one another and attached to the base plate in the same manner as described above in relation to the previous embodiments. As can be seen, the bracket of FIG. 4 employs a twill type mesh material. However, the first layer of mesh material 20 is 300 to 400 mesh, the second layer of mesh material 22 is 200 mesh, and the third layer of mesh material 24 is 100 mesh.

The bracket 10 of FIG. 4 therefore is constructed so that the openings of the mesh material become wider or, that is, the mesh becomes rougher from the base plate 18 to the outer layer of mesh material 24. It has been found that this ordering of the several layers of mesh material results in an increase in the strength of the bond between the bracket 10 and the surface of the tooth. However, upon removal of the bracket 10 from the tooth, this construction permits only minute amounts of adhesive material to remain on the surface of the tooth.

Figure 5:
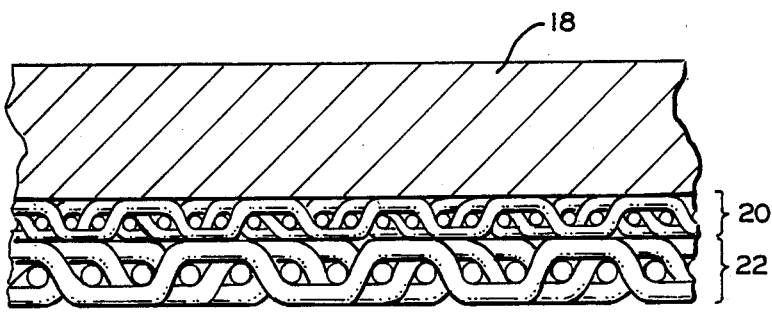
FIG. 5 is a partial cross-sectional view of another embodiment of the apparatus of the invention including two layers of mesh material.

In FIG. 5, yet another embodiment of the bracket 10 of the invention is shown. The bracket 10 of FIG. 5 however, includes only the two layers of mesh material 20 and 22. The layers of mesh material are superimposed on one another and attached to the base plate 18 in the same manner as described above in relation to the previous embodiments. The bracket 10 of FIG. 5 also employs a twill type of mesh material. The first layer of mesh material 20 is 200 mesh, and the second or outer layer of mesh material 22, is 100 mesh. This particular construction has also been found to provide an increased bonding strength between the bracket 10 and the surface of the tooth, yet permits only minute portions of adhesive material to remain on the tooth after removal of the bracket therefrom.

Although the apparatus of the invention has been described in several preferred embodiments, it will be understood that they may be modified without departing from the scope of the claims of the invention. For example, the bracket 10 may comprise at least two or more layers of mesh material. Additionally, the shape of the bracket 10 need not be limited to that shown in FIGS. 1 and 2. It is only necessary that the bracket 10 be of a type that can be directly attached to the surface of a tooth. Indeed, the invention contemplates the use of any type of orthodontic apparatus including, for example, buccal tubes and lingual appliances. Furthermore, any of a variety of materials may be employed for the layers of mesh material 20, 22 and 24, such as, for example, synthetic resin materials that may be attached to the outer surface of the base plate 18 by means of an adhesive. The specification and drawings are, accordingly, to be regarded in an illustrative rather than in a restrictive sense.

What is claimed is:

1. An orthodontic apparatus for attachment to a tooth, said apparatus comprising:
   a base portion,
   a base plate attached to said base portion, and
   a plurality of layers of mesh material superimposed on the outer surface of said base plate and attached thereto, each of said layers of mesh material providing a layer of interstitial passages, said apparatus being attachable to the surface of a tooth by applying an adhesive material to said plurality of layers of mesh material and bonding said plurality of layers of mesh material directly to the surface of the tooth.

2. The orthodontic apparatus of claim 1, wherein one of said layers of mesh material is a different mesh than at least one of said other layers of mesh material.

3. An orthodontic apparatus for attachment to a tooth, said apparatus comprising:
   a base portion,
   a base plate attached to said base portion, and
   a plurality of layers of mesh material superimposed on the outer surface of said base plate and attached thereto, wherein the mesh of said outermost layer of mesh material is finer than the mesh of each of said interior layers of mesh material, said apparatus being attachable to the surface of a tooth by applying an adhesive material to said plurality of layers of mesh material and bonding said plurality of layers of mesh material directly to the surface of the tooth.

4. An orthodontic apparatus for attachment to a tooth, said apparatus comprising:
   a base portion,
   a base plate attached to said base portion, and
   a plurality of layers of mesh material superimposed on the outer surface of said base plate and attached thereto, wherein the mesh of each said successive layer of mesh material in the direction from said base plate to said outermost layer of mesh material is finer than the mesh of said preceding layer of mesh material, said apparatus being attachable to the surface of a tooth by applying an adhesive material to said plurality of layers of mesh material and bonding said plurality of layers of mesh material directly to the surface of the tooth.

5. An orthodontic apparatus for attachment to a tooth, said apparatus comprising:
   a base portion,
   a base plate attached to said base portion, and
   three layers of mesh material superimposed on the outer surface of said base plate and attached thereto, wherein said first layer of mesh material is attached to said base plate and said third layer of mesh material is the outermost layer, said apparatus being attachable to the surface of a tooth by applying an adhesive material to said layers of mesh material and bonding said layers of mesh material directly to the surface of the tooth.

6. The orthdontic apparatus of claim 5, wherein
   said first layer of mesh material is approximately 100 mesh,
   said second layer of mesh material is approximately 200 mesh, and
   said third layer of mesh material is within the range of 300 to 400 mesh.

7. The orthodontic apparatus of claim 5, wherein each of said layers of mesh material is approximately 400 mesh.

8. The orthodontic apparatus of claim 5, wherein said first layer and said second layer of mesh material are each within the range of 100 to 200 mesh, and said third layer of mesh material is within the range of 300 to 400 mesh.

9. An orthodontic apparatus for attachment to a tooth, said apparatus comprising:
   a base portion,
   a base plate attached to said base portion, and
   a plurality of layers of mesh material superimposed on the outer surface of said base plate and attached thereto, wherein the mesh of said outermost layer of mesh material is rougher than the mesh of each of said interior layers of mesh material, said apparatus being attachable to the surface of a tooth by applying an adhesive material to said plurality of layers of mesh material and bonding said plurality of layers of mesh material directly to the surface of the tooth.

10. An orthodontic apparatus for attachment to a tooth, said apparatus comprising:
    a base portion,
    a base plate attached to said base portion, and
    a plurality of layers of mesh material superimposed on the outer surface of said base plate and attached thereto, wherein the mesh of each said successive layer of mesh material in the direction from said base plate to said outermost layer of mesh material is rougher than the mesh of said preceding layer of mesh material, said apparatus being attachable to the surface of a tooth by applying an adhesive material to said plurality of layers of mesh material and bonding said plurality of layers of mesh material directly to the surface of the tooth.

11. The orthodontic apparatus of claim 5, wherein
said first layer of mesh material is in the range of 300 to 400 mesh,
said second layer of mesh material is approximately 200 mesh, and
said third layer of mesh material is approximately 100 mesh.

12. An orthodontic apparatus for attachment to a tooth, said apparatus comprising:
a base portion,
a base plate attached to said base portion, and
two layers of mesh material superimposed on the outer surface of said base plate and attached thereto, wherein said first layer of mesh material is attached to said base plate and said second layer of mesh material is the outermost layer, said apparatus being attachable to the surface of a tooth by applying an adhesive material to said plurality of layers of mesh material and bonding said plurality of layers of mesh material directly to the surface of the tooth.

13. The orthodontic apparatus of claim 12, wherein
said first layer of mesh material is approximately 200 mesh, and
said second layer of mesh material is approximately 100 mesh.

14. A base member for attaching an orthodontic apparatus to a tooth, said base member comprising:
a base plate, said base plate defining on one side thereof an outer surface for attaching an orthodontic apparatus thereto, said base plate further defining on an opposite side thereof an inner surface for attaching mesh material thereto; and
at least two layers of mesh material, said layers of mesh material being superimposed on said inner surface of said base plate and attached thereto, each of said layers of mesh material providing a layer of interstitial passages, said base member being attachable to a tooth by applying adhesive material to said layers of mesh material for bonding said base member to a tooth.

15. A base member as defined in claim 14, wherein
one of said layers of mesh material is a different mesh than at least one of said other layers of mesh material.

16. A base member as defined in claim 15, wherein
at least one of said layers of mesh material is finer than 100 mesh.

17. A base member as defined in claim 14, wherein
one of said layers of mesh material has a different mesh construction than at least one of said other layers of mesh material.

18. A base member as defined in claim 17, wherein
at least one of said layers of mesh material is a plain fabric-type mesh and at least one of said other layers of mesh material is a twill-type mesh.

19. A base member as defined in claim 14, said base member comprising:
three of said layers of mesh material, said first layer of mesh material being attached directly to said inner surface of said base plate and said third layer of mesh material being the outermost layer.

20. A base member as defined in claim 19, wherein
said first and second layers of mesh material are each in the range of 100 to 200 mesh, and said third layer of mesh material is in the range of 300 to 400 mesh.

21. A base member as defined in claim 19, wherein
said first layer of mesh material is in the range of 300 to 400 mesh, said second layer of mesh material is approximately 200 mesh, and said third layer of mesh material is approximately 100 mesh.

* * * * *